United States Patent

Leichtling et al.

[11] Patent Number: 5,336,230
[45] Date of Patent: Aug. 9, 1994

[54] ENDOSCOPIC SUTURE TYING METHOD

[75] Inventors: Jonathan J. Leichtling, San Francisco, Calif.; Charles S. Taylor, 4380 - 26th St., San Francisco, Calif. 94131

[73] Assignee: Charles S. Taylor, San Francisco, Calif.

[21] Appl. No.: 971,896

[22] Filed: Nov. 4, 1992

[51] Int. Cl.⁵ .................................................. A61B 17/00
[52] U.S. Cl. .................................... 606/148; 606/139; 606/205; 128/898
[58] Field of Search .............. 606/120, 139, 144, 145, 606/147, 148, 151, 205–208, 210–211; 128/898

[56] References Cited

U.S. PATENT DOCUMENTS

| | | | |
|---|---|---|---|
| 2,012,776 | 8/1935 | Roeder | 606/139 |
| 2,316,297 | 4/1943 | Southerland et al. | 606/139 |
| 2,518,994 | 8/1950 | Miller | 606/205 |
| 3,244,342 | 4/1966 | Boorlakov et al. | |
| 3,496,940 | 2/1970 | Steinman | |
| 3,515,129 | 6/1970 | Truhan | |
| 3,623,212 | 11/1971 | Child | |
| 3,633,582 | 1/1972 | Steinman | |
| 3,763,548 | 10/1973 | Anderson | |
| 3,781,969 | 1/1974 | Anderson | |
| 3,800,403 | 4/1974 | Anderson et al. | |
| 3,959,960 | 6/1976 | Santos | |
| 4,345,601 | 8/1982 | Fukuda | |
| 4,635,638 | 1/1987 | Weintraub et al. | |
| 4,755,181 | 7/1988 | Igoe | |
| 4,827,931 | 5/1989 | Longmore | |
| 4,932,962 | 6/1990 | Yoon et al. | |
| 5,037,433 | 8/1991 | Wilk et al. | 606/139 |
| 5,100,421 | 3/1992 | Christoudias | 606/147 |
| 5,144,961 | 9/1992 | Chen et al. | 128/898 |
| 5,147,373 | 9/1992 | Ferzli | 606/148 |
| 5,196,023 | 3/1993 | Martin | 606/148 |
| 5,203,863 | 4/1993 | Bidoia | 606/139 |
| 5,211,655 | 5/1993 | Hasson | 606/205 |
| 5,234,443 | 8/1993 | Phan et al. | 606/205 |

OTHER PUBLICATIONS

"Endoscopic Knot Tying Manual" by Ethicon, 1991, pp. 1, 15–26.

Primary Examiner—Stephen C. Pellegrino
Assistant Examiner—Jeffrey A. Schmidt
Attorney, Agent, or Firm—Flehr, Hohbach, Test, Albritton & Herbert

[57] ABSTRACT

Endoscopic suture tying apparatus adapted to be grasped by the hand for use in a laparoscopic procedure with an introducer device extending into the body of a patient having a sleeve with a bore therein extending therethrough into the body of the patient. A holding sleeve is provided which is sized so that it can be introduced through the bore of the introducer device. First and second grasping devices are provided which are mounted in the holding sleeve. Each of the grasping devices is comprised of a hollow tubular member having a bore therein and a push-pull rod slidably mounted in the bore in the tubular member. The outer tubular member has proximal and distal extremities. First and second jaws are provided which are secured to the distal extremity of the tubular member. The jaws are movable between open and closed positions with respect to each other. The outer sleeve and the rod are connected to the first and second jaws whereby upon relative movement between the outer sleeve and the rod the first and second jaws are moved between said open and closed positions. Handles are secured to the proximal extremity of the outer sleeve and to the proximal extremity of the rod for causing the relative movement between the tubular and the rod.

2 Claims, 3 Drawing Sheets

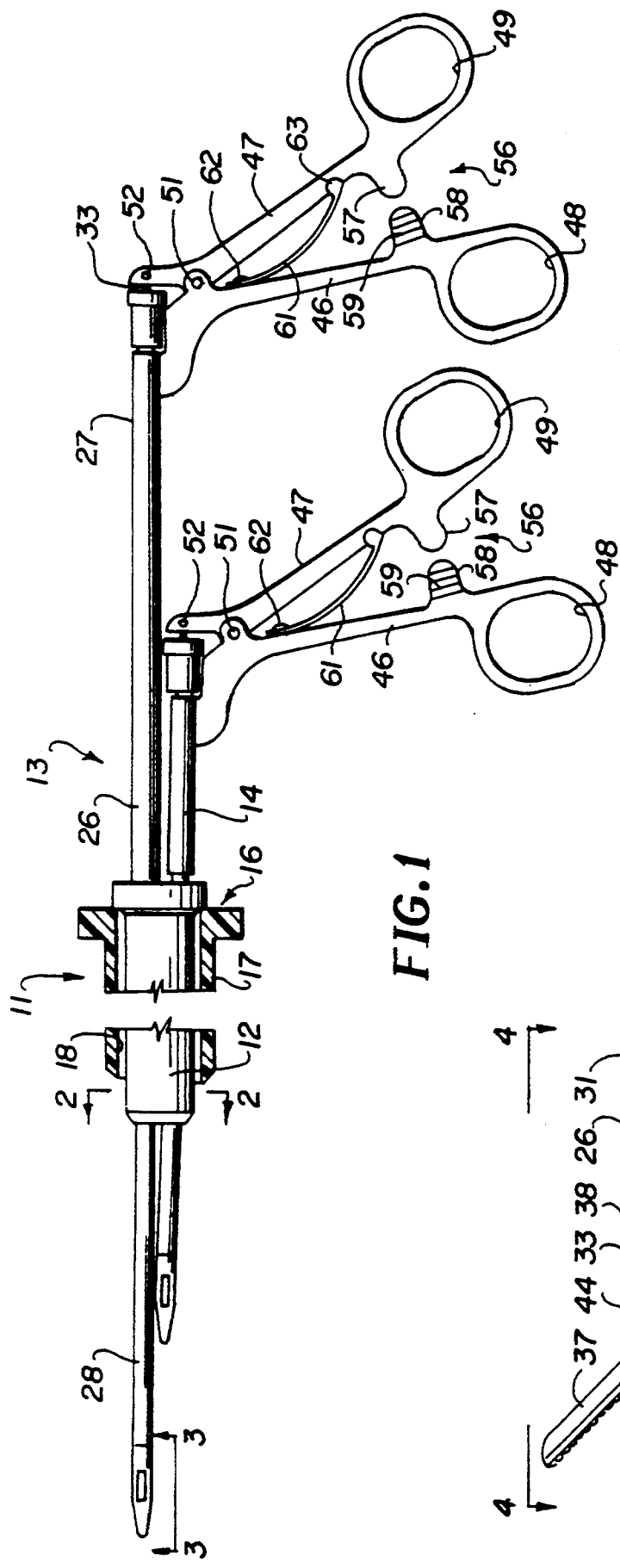

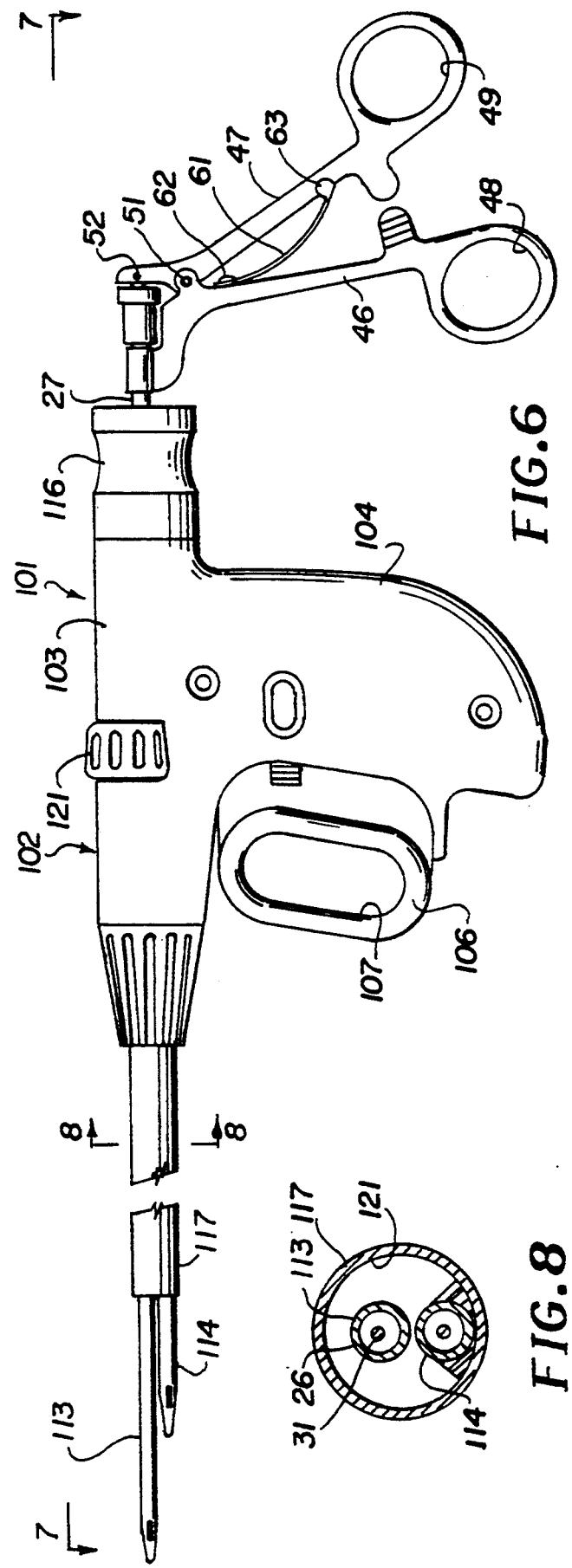
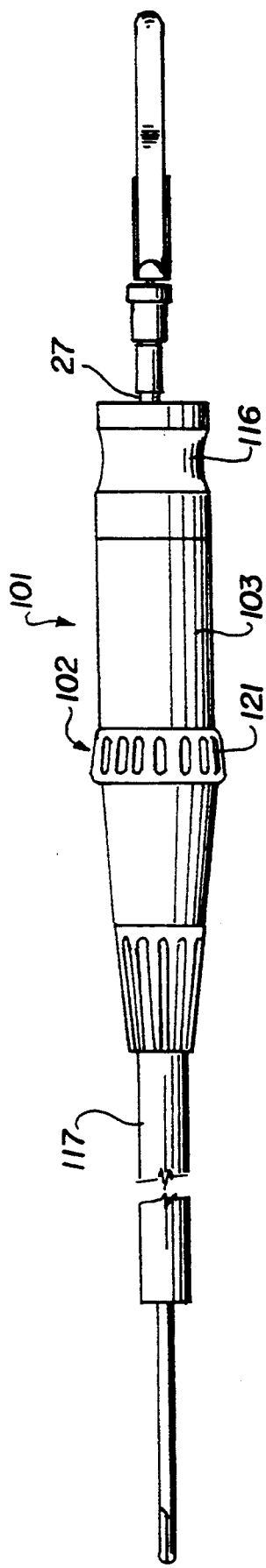

ENDOSCOPIC SUTURE TYING METHOD

This invention relates to an endoscopic suture tying apparatus and method, and more particularly to such an apparatus and method which is particularly adapted for use in laparoscopic procedures.

In laparoscopic procedures, the tying of knots in sutures has been very difficult and time consuming. In certain procedures utilized in the past, two independent tools have been utilized in which one holds the needle and the other holds the thread. In other procedures, the suture to be tied has been brought out through a cannula and then a knot is formed externally of the cannula. The knot is then taken down into the cannula to the location where the knot is desired. It can be readily seen that such devices and procedures are very time consuming. There is therefore a need for a new and improved endoscopic suture-tying apparatus and method which overcomes these disadvantages.

In general, it is an object of the present invention to provide an endoscopic suture tying apparatus and method which is particularly adapted for use in laparoscopic procedures.

Another object of the invention is to provide an apparatus and method of the above character which can be expeditiously used for tying knots.

Another object of the invention is to provide an apparatus and method of the above character in which the knot-tying procedure can be learned within a relatively short period of time.

Additional objects and features of the invention will appear from the following description in which the preferred embodiments are set forth in detail in conjunction with the accompanying drawings.

FIG. 1 is a side elevational view of an endoscopic suture tying apparatus incorporating the present invention.

FIG. 2 is a cross-sectional view taken along the line 2—2 of FIG. 1.

FIG. 3 is an enlarged view taken along the line 3—3 of FIG. 1 showing the jaws in an open position.

FIG. 4 is a top plan view looking along the line 4—4 of FIG. 3.

FIG. 6 is a side elevational view of another embodiment of the endoscopic suture-tying apparatus incorporating the present invention.

FIG. 7 is a top plan view of the apparatus shown in FIG. 6 looking along the line 7—7 of FIG. 6.

FIG. 8 is a cross-sectional view taken along the line 8—8 of FIG. 6.

Figure 5A:
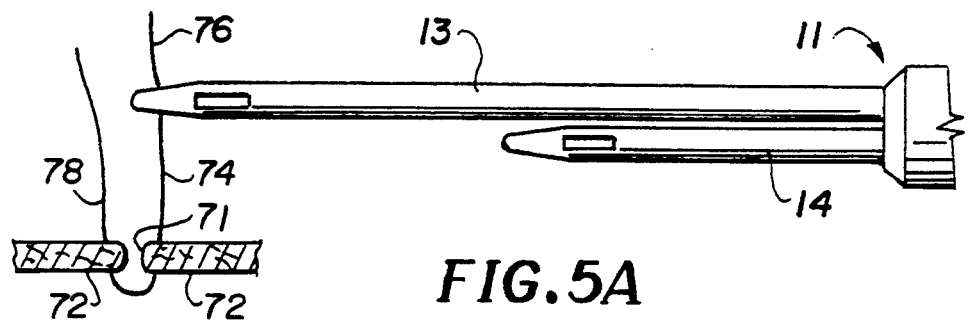
FIGS. 5A through 5H show the apparatus of the present invention utilizing the method of the present invention to tie a knot in a suture.

In general, the endoscopic suture-tying apparatus is adapted to be grasped by the hand for use in a laparoscopic procedure with an introducer device extending into the body of a patient and having a sleeve with a bore extending therethrough into the body of the patient. The apparatus is comprised of a holding sleeve sized so that it can be introduced through the bore of the introducer device. First and second grasping devices are slidably mounted in the holding sleeve for relative co-linear movement therein. Each of the grasping devices is comprised of an outer tubular member having a bore therein and a push-pull rod slidably mounted in the bore in the tubular member. The tubular member is provided with proximal and distal extremities. First and second jaws are secured to the distal extremity of the tubular member. The first and second jaws are movable between open and closed positions with respect to each other. Means is provided which connects the outer sleeve and the rod to the first and second jaws, whereby upon relative movement between the outer sleeve and the rod the first and second jaws are moved between said open and closed positions. Means is secured to the proximal extremity of the outer sleeve and to the rod and adapted to be grasped by the hand for causing said relative movement between said outer sleeve and said rod.

More in particular as shown in FIGS. 1 through 4 of the drawings, the endoscopic suture-tying apparatus 11 consists of a holding sleeve 12 which has first and second grasping devices 13 and 14 co-linearly mounted therein. The holding sleeve 12 is adapted to be introduced through an introducer device 16 typically called a cannula, which is provided with a sleeve 17 having a bore 18. The external diameter of the holding sleeve 12 is sized so that it can readily slide into the bore 18 of the introducer sleeve 16. Typically, the introducer device 16, when it is in the form of a cannula, can be used for puncturing the body of the patient, as for example the abdomen for performing a laparoscopic procedure in such a manner so that the bore in the sleeve 17 opens into the body of the patient.

The holding sleeve 12 can be formed of a suitable material such as metal or plastic. If formed of metal, as shown in FIG. 2, an insert 21 can be provided within the cylindrical bore 22 and is frictionally retained therein. The insert 21 is provided with longitudinally extending passages 23 and 24 extending the length of the holding sleeve 12 and which can be generally vee-shaped in cross-section, as shown particularly in FIG. 2.

The grasping devices 13 and 14 extend through the passages 23 and 24 and are frictionally retained within the holding sleeve 12 by frictional engagement with the insert 21 forming the passages 23 and 24.

The first and second grasping devices 13 and 14 are constructed in a similar manner with the exception that grasping device 13 is provided with a longer shaft than that of the grasping device 14. The grasping device 13 is comprised of an outer tubular member 26 formed of a suitable metal such as brass or stainless steel. The tubular member 26 is provided with proximal and distal extremities 27 and 28. The tubular member 26 is provided with a bore 29 extending the length thereof. A push-pull rod 31 is slidably mounted in the bore 29 and extends the length of the tubular member 26. The push-pull rod 31 is provided with proximal and distal extremities 32 and 33. The rod 31 also can be formed of a suitable metal such as stainless steel or brass.

The tubular member 26 and the push rod 31 can have a suitable length, as for example 16 to 18 inches. First and second jaws 36 and 37 are carried by the distal extremity 28 of the tubular member 26 and are movable between open and closed positions with respect to each other for serving as a grasper. Thus, as shown particularly in FIG. 3, the first jaw is a fixed jaw and is mounted in a fixed position on the distal extremity 33 of the tubular member 26, as for example by brazing it to the distal extremity 28 along the line 38. The second jaw 37 is pivotally mounted in a slot 41 provided in the first jaw 36 by a fixed pivot pin 42 extending through the fixed jaw. Means is provided for pivotally connecting the second removable jaw 37 to the distal extremity 33 of the rod 31 and consists of a pin 43 mounted in the jaw 37 and having mounted thereon an eye 44 provided on the distal extremity 33 of the rod 31.

Thus it can be seen that by causing relative movement between the rod 31 and the outer sleeve 26, the jaws 36 and 37 can be moved between open and closed positions with respect to each other. Handle means adapted to be grasped by the hand is secured to the proximal extremities of the outer tubular member 26 and the rod 31 to cause movement of the rod 31 with respect to the tubular member 26 to cause the opening and closing of jaws 36 and 37. The handle means consists of scissors-type handles 46 and 47 which are provided with finger loops 48 and 49 adapted to be grasped by the fingers of a human hand. The handle members 46 and 47 are pivotally connected to each other by a pivot pin 51. The handle member 46 is secured to the proximal extremity 27 of the tubular member 26, whereas handle member 47 is pivotally connected to the proximal extremity 33 of the push-pull rod 31 by suitable means such as by a pin 52 extending through the proximal extremity 33 of the push-pull rod 31.

A serrated latching mechanism 56 is provided on the handle members 46 and 47 and takes the form of tabs 57 and 58 provided on the handle members 46 and 47, and which are provided with serrations 49 on opposite sides thereof so that when the tabs 57 and 58 overlie each other the serrations will grasp each other to latch the handle members 46 and 47 in a closed position to be retained in the closed position until they are separated by movement of the finger rings 48 and 49 by the hands of the physician. Springs means is provided for preventing inadvertent latching of the latching mechanism 56 carried by the handle members 46 and 47, and consists of a leaf spring 61 which has one end secured to the handle member 46 by a rivet or a screw 62 and has the other end provided with a U-shaped saddle 63 which is adapted to engage a lower extremity of the handle 47 to yieldably urge the handle 47 away from the handle 46.

The second grasping device 14 is constructed in a manner which is very similar to that of the grasping device 13, therefore the same numerals have been applied to the corresponding components.

Operation and use of the endoscopic suture-tying apparatus 11 may now be briefly described as follows in performing the method of the present invention. Let it be assumed that a laparoscopic procedure is underway within the abdomen and that a cannula has been inserted through the abdomen of the patient, such as by the use of the cannula 16 which is provided with the bore 18 therein. Thus, as shown in FIG. 5A, let it be assumed that an incision 71 has been made in the tissue 72 within the abdomen and it is desired to close the incision by the use of a suture 74. Also let it be assumed that the suture 74 has been passed through the margin of the tissue 72 abutting the incision 71 by a needle in a suitable manner such as by the use of an endoscopic needle holder as the type described in co-pending application Ser. No. 07/971,279, filed Nov. 4, 1992. In this way, the suture is passed through the tissue on one side of the incision 71 and then brought up through the tissue 72 on the other side of the incision as shown in FIG. 7A to provide a U-shaped configuration for the suture 74. Once the suture 74 has been placed through the two edges of the tissue 72 abutting the incision 71, normally it is desirable to pull the two edges of the tissue together so they abut to form a butt joint with the two edges of the tissue coming together in contact with each other to promote healing of the incision and to cause tissue to grow together.

Figure 5B:
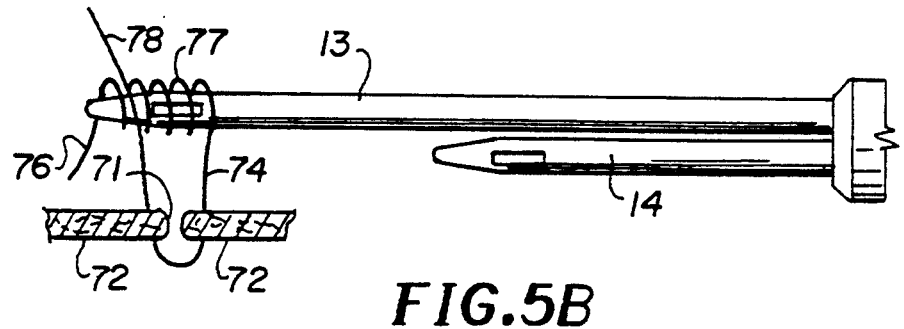

Let it be assumed that it is now desired to tie a knot in the suture to form a butt joint between the tissue 72 by the use of the endoscopic suture-tying apparatus of the present invention. The apparatus 11 is introduced through the bore 18 of the introducer device 16 by the physician grasping the finger loops 48 and 49 of the grasping device 13. After the apparatus 11 has been introduced into the abdomen of the patient, the grasping devices 13 and 14 are advanced with their jaws in closed positions. The surgeon while viewing the procedure through an endoscope provided in another location in the abdominal cavity advances the suture-tying apparatus 11 with the jaws of the grasping devices 13 and 14 in closed positions so that it is seated within the introducer device 16. The distal extremity of the first grasping device 13 is advanced into the vicinity of the suture or thread 17. The finger loops 48 and 49 are operated by the hand of the surgeon to open the first jaw 36 with respect to the second jaw 37 and then advancing the same over the free end 76 of the suture. The finger loops 48 and 49 then are moved together by the surgeon to clamp the free end 76 between the jaws 36 and 37. The grasping device 13 is then rotated in either a counterclockwise or clockwise direction, as for example in a clockwise direction as shown in FIG. 5B, to wrap the suture 74 therein in a helical fashion to provide a plurality of wraps 77 which are spaced apart towards the proximal end of the grasping device 13. A suitable number of wraps, as for example four as shown in FIG. 5B, can be provided. However, it should be appreciate that depending on the desires of the surgeon, one to five wraps can be provided.

Figure 5C:
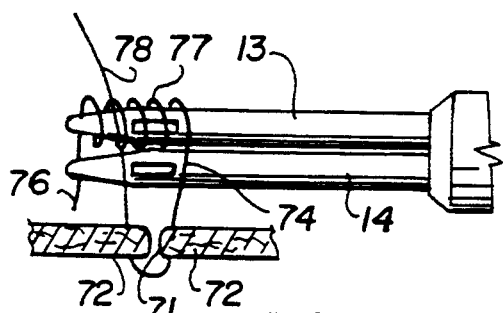
Figure 5D:
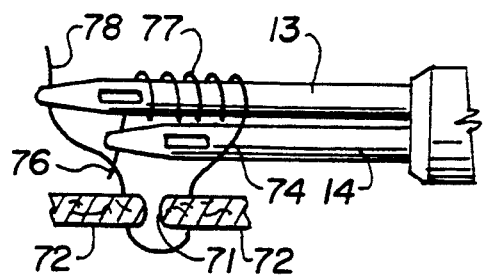
Figure 5E:
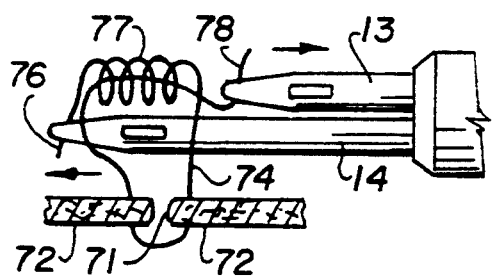
Figure 5F:
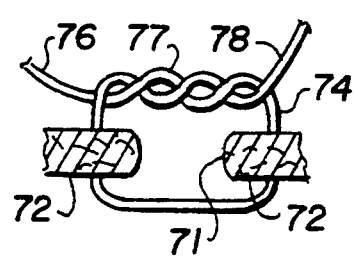
Figure 5G:
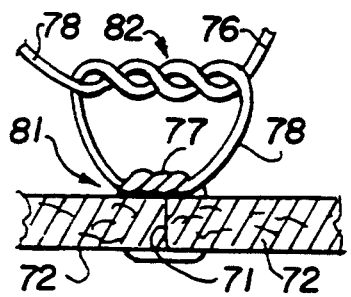
Figure 5H:
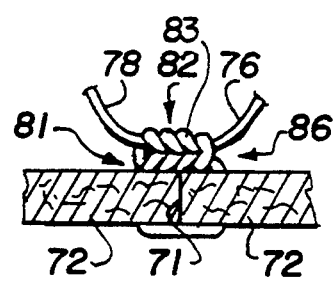

The grasping device 14 is then utilized and its jaws opened by having the surgeon use his other hand to grasp the finger loops 48 and 49 of that device, or shifting the hand utilized for the first grasping device 13 to the second grasping device 14 to cause the jaws 36 and 37 to be opened and to grasp the free end 76 which extends from the jaws 36 and 37 of the first grasping device 13 as shown in FIG. 5C. The jaws 36 and 37 of the first grasping device 13 are then opened to permit the free end 76 to be released therefrom and so that it is retained only by the jaws of the second grasping device 14. The first grasping device 13 is then utilized to grasp the free end 78 of the suture 74 by closing the jaws on the free end 78 and retain the same therein as shown in FIG. 5D. The first grasping device 13 is then retracted as shown in FIG. 5E to draw the free end 78 of the suture 74 through the wraps or multiple loops 77 as shown in FIG. 5E. This constitutes the formation of a first layer 81 of a conventional surgeon's knot which is similar to a half-hitch knot repeated four times like the four half-hitches as shown in FIG. 5F. Thereafter, the first and second grasping devices 13 and 14 are actuated to pull on the two free ends 76 and 78 to bring the edges of the tissue 72 into close proximity to each other to form a butt joint as shown in FIG. 5G and to form a tight first layer 81 of a conventional surgeon's knot as shown in FIG. 5H.

The same procedure as hereinbefore described is utilized with the exception that the wraps 82 which form second layer 83 are wound in an opposite direction of the wraps 77. The free ends 76 and 78 are then tightened by use of the grasping devices 13 and 14 to form a second layer 83 which is stacked on top of the layer 81 to cause a cinching action to take place to form a completed knot 81.

Additional knots 86 can be formed along the length of the incision 71 to completely close the incision. After the knot-tying operations have been completed, the endoscopic suture-tying apparatus 11 can be removed. Thereafter, the other apparatus utilized in connection with the laparoscopic procedure can be removed and the incisions formed in the abdomen can be closed in a conventional manner.

Another embodiment of the endoscopic suture-tying apparatus incorporating the present invention is shown in FIGS. 6 through 8 and, as shown therein, the endoscopic suture-tying apparatus 101 incorporates the use of a gun-handle-type device 102 of the type described in co-pending application Ser. No. 07/806,666, filed Dec. 31, 1991. As described therein, the device consists of a housing 103 which has a depending gun-type handle or pistol grip 104 depending therefrom which is provided with a trigger 106 having a large finger hole 107 extending therethrough.

First and second grasping devices 113 and 114 are provided which are very similar to the grasping devices 13 and 14 hereinbefore described. The second grasping device 114 is secured to a fitting 116 of the type described in co-pending application Ser. No. 07/806,666, filed Dec. 31, 1991, which is adapted to be inserted into the barrel through the housing 103. The distal extremity of the grasping device 114 can be rotated by the knob 121 provided in the housing 103 and the jaws can be opened and closed by actuation of the trigger 106. The grasping device 113 can be inserted through the bore (not shown) of the bore 121 of the barrel 117. As shown, the grasping device 113 is provided with the conventional scissors-type handles hereinbefore described for operating the jaws.

The apparatus as shown in FIGS. 6 through 8 can be utilized in the same manner as the apparatus shown in FIGS. 1 through 4 for tying a knot in the manner hereinbefore described. The apparatus shown in FIGS. 6 through 8, as well as the apparatus in FIGS. 1 through 4, can be utilized by a surgeon whether he is right-handed or left-handed. Thus, by way of example, if the surgeon is right-handed, the pistol grip or handle 104 can be grasped by the right hand of the surgeon while the other left hand is utilized to operate the scissors-type handle provided as a part of the grasping device 113.

In view of the foregoing, it can be seen that there has been provided an endoscopic suture-tying apparatus which can be utilized in laparoscopic procedures for facilitating the tying of knots in sutures. A single apparatus can be provided extending through a single introducer device for accomplishing the knot-tying operation. In addition, the knots, with relatively little training, can be tied by a surgeon rather quickly. With only a little bit of experience, a surgeon can tie a knot of the type hereinbefore described within a short period of time, as for example from 1 to 3 minutes, with very little difficulty. The knots formed are tightly cinched.

What is claimed is:

1. A method for tying a knot in a suture, comprising providing an endoscopic suture-tying apparatus comprised of a holding sleeve having first and second grasping devices slidably mounted in the holding sleeve and having a grasper at the distal extremity thereof, providing a suture having first and second free ends, using the first grasping device to grasp the first free end, rotating the first grasping device grasping the first free end to form a plurality of helical wraps around the first grasping device, using the second grasping device to grasp the first free end of the suture retained by the first grasping device, operating the first grasping device to release the first free end from the first grasping device, using the first grasping device to grasp the second free end, moving the first grasping device to move the second free end through the helical wraps, moving the first and second grasping devices to pull on the first and second free ends to tighten the helical wraps to form at least a portion of a knot.

2. A method as in claim 1 together with the additional steps of grasping the first free end with the first grasping device, rotating the first grasping device to form helical wraps extending in an opposite direction from the first named helical wraps formed, manipulating the second grasping device to grasp the first free end of the suture being retained by the first grasping device, operating the first grasping device to release the first free end from the first grasping device, operating the first grasping device to grasp the second free end, moving the first grasping device to bring the second free end through the helical wraps formed in said opposite direction, moving the first and second grasping devices to pull on the first and second free ends to tighten the helical wraps extending in said opposite direction to bring them close together and to come into contact with the first named wraps to form a cinched knot.

* * * * *